United States Patent [19]

Focht

[11] Patent Number: 5,414,556
[45] Date of Patent: May 9, 1995

[54] SECURING AND LOCKING ASSEMBLY FOR LIVE CELL CHAMBERS

[76] Inventor: Daniel C. Focht, 334 Heist Rd., Butler, Pa. 16001

[21] Appl. No.: 38,241

[22] Filed: Mar. 29, 1993

[51] Int. Cl.⁶ .................................................. G02B 21/34
[52] U.S. Cl. ..................................... 359/398; 356/246
[58] Field of Search ................ 359/395, 398; 356/246, 356/244

[56] References Cited

U.S. PATENT DOCUMENTS

| | | | |
|---|---|---|---|
| 3,726,597 | 4/1973 | Dvorak et al. | 356/244 |
| 4,807,594 | 2/1989 | Chatenever | 128/4 |
| 4,974,952 | 12/1990 | Focht | 359/398 |
| 5,054,886 | 10/1991 | Ozaki et al. | 359/823 |
| 5,181,382 | 1/1993 | Middlebrook | 62/3.2 |
| 5,257,128 | 10/1993 | Diller et al. | 359/395 |

FOREIGN PATENT DOCUMENTS 1485186   6/1989   U.S.S.R. ................ 359/398

Primary Examiner—Joseph A. Popek
Assistant Examiner—Andrew Q. Tran

[57] ABSTRACT

A securing and locking assembly for live cell chambers includes a ring shaped unit received in a circular shaped chamber base to be secured with an upper circular shaped chamber frame unit. The ring unit is rotatable over a limited arcuate distance, and includes four L-shaped fingers space 90° apart and arranged to be received outside four 90° spaced radially extending peripheral recesses formed in the upper chamber unit. Upon rotation of the ring unit a predetermined arcuate distance the fingers are positioned outside the recesses of the upper chamber frame unit and upon continuing rotation of yet another predetermined arcuate distance the upper portions of the fingers engage upper portions of the chamber frame unit to uniformly secure and lock the chamber base and upper chamber unit together. Rotating the ring unit in the opposite direction will result in the unlocking of the chamber base and the upper chamber unit from each other.

5 Claims, 3 Drawing Sheets 5,414,556

SECURING AND LOCKING ASSEMBLY FOR LIVE CELL CHAMBERS

BACKGROUND OF THE INVENTION

This invention relates to a securing and locking assembly for live cell chambers for use with light microscopes.

Live cell chambers, typical of which is mine described in my U.S. Pat. No. 4,974,952, issued to me on Dec. 4, 1990, include an upper chamber frame unit and a lower chamber base operatively engaging the upper chamber frame unit. A chamber or enclosure is defined when the chamber frame unit and chamber base are secured. As more fully described and illustrated in my said Patent, included within the enclosure are an upper seal unit, a fragile cover slip, an infusion/perfusion unit, and a lower gasket or gaskets. An infusion/perfusion chamber is formed between the cover slip unit, the lower gasket, and the infusion/perfusion unit. With the elements of the live cell chamber secured in place it is ready for use, as described, with an appropriate light microscope.

A heretofore manner of securing chamber frame units to mating chamber bases was by use of machine screws received in threaded openings. The chamber frame units would thereby be secured and locked in place with the chamber bases. The machine screw arrangement of locking the elements in place demonstrated certain problems. Overtightening the screws resulted in breakage of infusion/perfusion units or other microscope slides used in the assemblies. Also, overtightening or uneven tightening the machine screws resulted in strain in the glass elements because of a resulting uneven arrangement of cover slips and slide units. It was also found that leakage ziones resulted between chamber frame units and chamber bases due to uneven tightening of the machine screws. Uneven arrangements of chamber frames and chamber bases also created uneven stress on the internal glass elements causing undesirable optical effects. When the surfaces of the internal glass elements of the live cell chamber were not parallel resulting from the uneven tightening of the external parts, undesirable optical cavities were formed between those glass elements.

The problems resulting in improper securing and joining of the chamber frame units and chamber bases generally resulted in ineffective live cell chambers given to providing faulty results in their uses. To prevent the aforesaid problems careful machine screw tightening procedures were encouraged. The tightening procedures did not, however, insure eliminating of the problems, mainly because the possibility of human error in following the procedures were not eliminated.

The securing and locking assembly of my present invention overcomes the heretofore problems associated with hand tightening of machine screws to secure and lock together chamber frame units and chamber bases, by providing uniform and positive securing and locking without the possibility of over-tightening or non-uniform tightening. By so providing, my invention prevents and eliminates leakage between the engaged interfaces of the chamber frame units and chamber bases, slide breakage, strain in the glass elements, and optical cavities due to uneven arrangement therebetween. The new results and advantages of the securing and locking assembly of my present invention are achieved with a simple combination of elements operable without the need of any tools or other aids.

SUMMARY OF THE INVENTION

This invention is a securing and locking assembly for live cell chambers. Typically, the live cell chambers include a chamber frame unit; a chamber base operatively engaging the chamber frame unit and forming an enclosure therewith; and cover slip windows and sealing units operatively associated with each other to form a live cell chamber. One such live cell chamber includes within the enclosure an upper seal unit operatively engaging the chamber frame unit, a cover slip unit operatively associated with the chamber base, an infusion/perfusion unit operatively associated with the cover slip, and lower gasket means operatively disposed intermediate the cover slip and the infusion/perfusion unit. The securing and locking assembly of this invention preferably comprises: rotatable securing means operatively engaging the chamber frame unit and the chamber base for uniformly securing and locking the chamber frame unit and the chamber base together upon rotation thereof through a predetermined arcuate distance and for unlocking the chamber frame unit and the chamber base upon reverse rotation the same arcuate distance. The securing means may be a rotatable ring unit received and supported by the chamber base, with the ring unit including uniformly spaced upwardly extending L-shaped fingers. A circular chamber frame unit may be provided with uniformly spaced radially extending peripheral recesses or notches shaped and sized such that the L-shaped fingers are positioned radially outside of the recesses. The ring unit is rotatable by hand and when rotating it the sides of the fingers will engage radial portions of openings through the chamber base. At that position the fingers will be arranged arcuately from the recesses with the upper legs of the fingers over the upper surface portions of the chamber frame unit. Continuing rotation of the ring unit results in uniform, simultaneous locking engagement by the fingers of upper portions of the chamber frame arcuately adjacent the recesses. Reverse rotation of the ring engagement will result in simultaneous disengagement of the fingers from the upper surface of the chamber frame unit and positioning of the fingers outside of the recesses to allow separation of the chamber frame unit and chamber base. The positive and uniform clamping and locking performance of the securing and locking assembly of the present invention eliminates the aforesaid problems inherent in the heretofore methods of joining and securing chamber frame units to chamber bases.

Various other advantages, details, and modifications of the present invention will become apparent as the following description of a certain present preferred embodiment proceeds.

DESCRIPTION OF THE DRAWINGS

In the accompanying drawings I show a certain present preferred embodiment of my invention in which.

DESCRIPTION OF A PREFERRED EMBODIMENT

Figure 1:
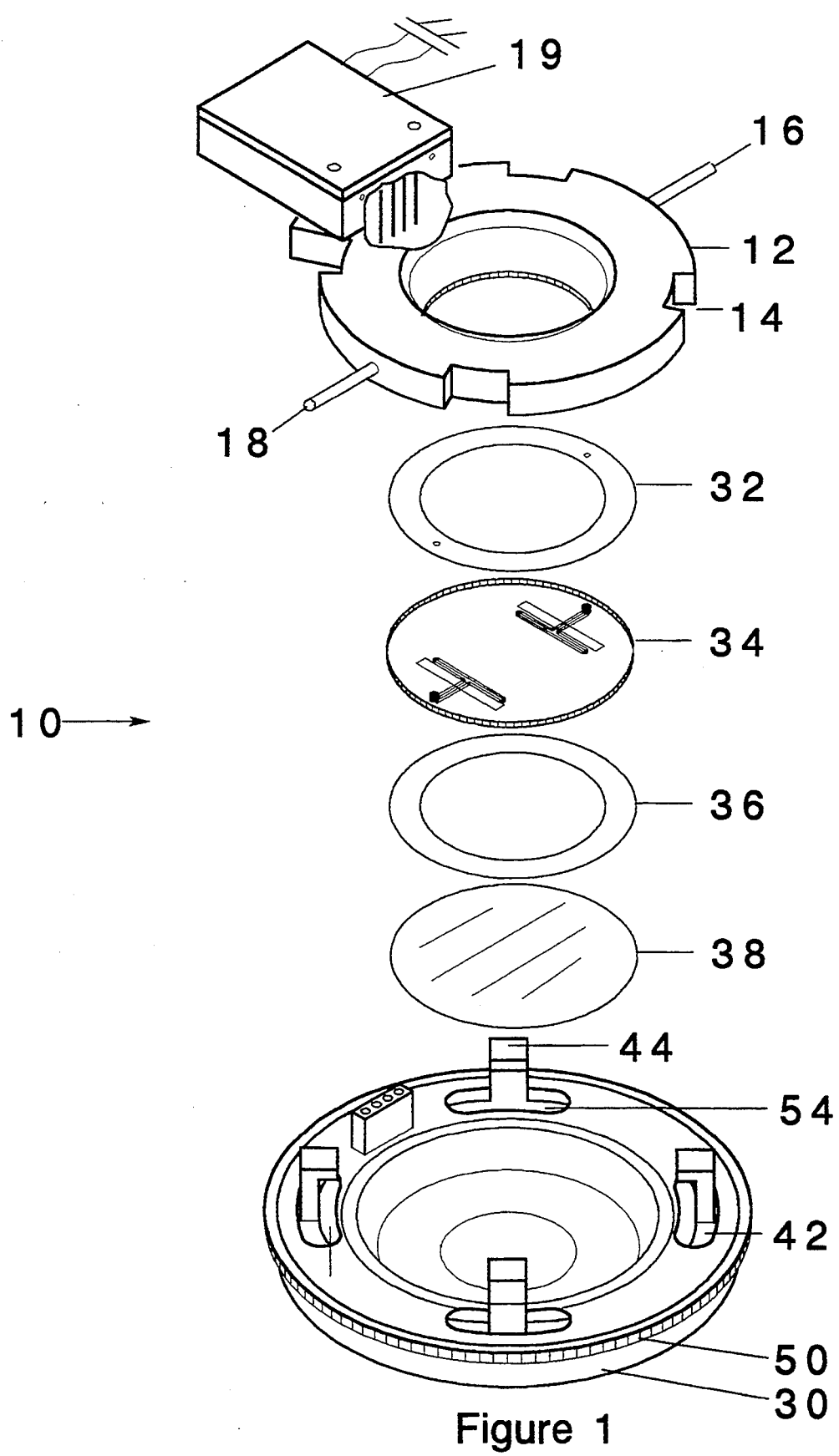
FIG. 1 is an exploded perspective view of an inverted version of a live cell chamber construction embodying the securing and locking assembly of the present invention.

Referring now to the drawings there is shown a typical live cell chamber 10 embodying the securing and locking assembly of the present invention. The live cell chamber 10 is substantially the same in its primary elements and function as the live cell chamber described and claim in my U.S. Pat. No. 4,974,952 issued on Dec. 4, 1990. It is to be understood, however, that the present invention is not limited to application with the live cell chamber of the Patent but, rather, is applicable to any live cell chamber. The basic and primary elements of the live cell chamber 10 shown in the drawings will be briefly described with the understanding that the more specific details of the elements and their respective functions may be found in U.S. Pat. No. 4,974,952.

Figure 2:
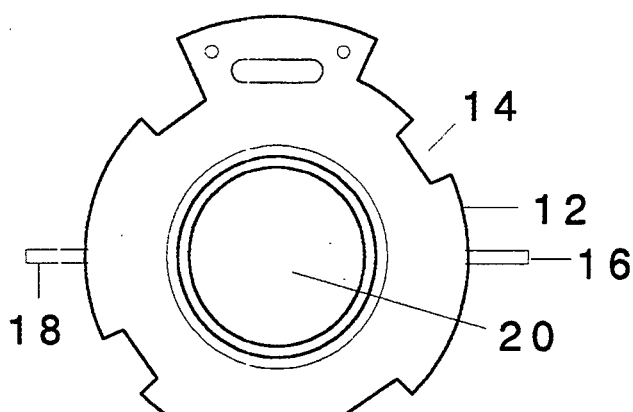
FIG. 2 is a plan view of the chamber frame unit of FIG. 1 showing certain details thereof not illustrated in FIG. 1.
Figure 4:
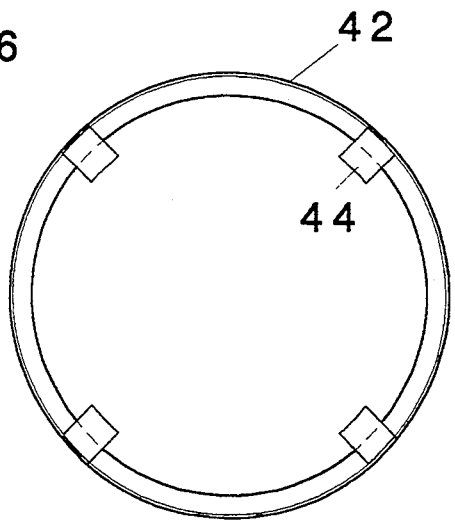
FIG. 4 is a plan view of one element of the rotatable ring assembly of the securing and locking assembly of the present invention, showing details not illustrated in FIG. 1.
Figure 3:
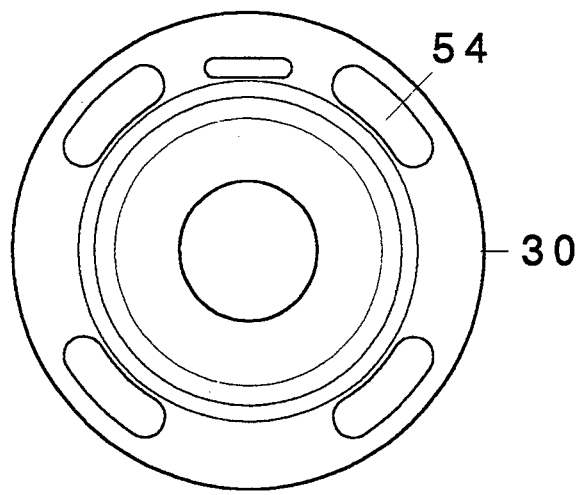
FIG. 3 is a plan view of the chamber base of FIG. 1 showing certain details not illustrated in FIG. 1.

As shown throughout the various drawings, live cell chamber 10 is an inverted microscope chamber with it to be understood that the present invention is not limited thereto and is applicable to an upright microscope chamber as well. The live cell chamber 10 includes an upper chamber frame unit 12 shown diagrammatically in FIG. 1 and in more specific detail in FIG. 2 and 3, the chamber frame unit being disc- or circular-shaped having formed therearound four generally identically shaped radially extending uniformly spaced recesses or notches 14 generally arcuately spaced 90° about the circumference of the chamber frame unit. Fluid ports 16 and 18 are provided for allowing infusion/perfusion and discharge of any desired culture medium through the chamber. The body of the chamber frame unit 12 is adapted to support a housing 19 for electrical connectors and the like for heaters and temperature sensors arranged within the confines of the assembled live cell chamber 10. The chamber frame unit 12 is also provided with an enlarged central operature 20, and is generally shaped to mate with a disc-shaped, generally circular support base unit or chamber base unit 30 of greater diameter than that of the chamber frame unit 12, for supporting and housing the remaining elements of the live cell chamber 10.

Figure 12:
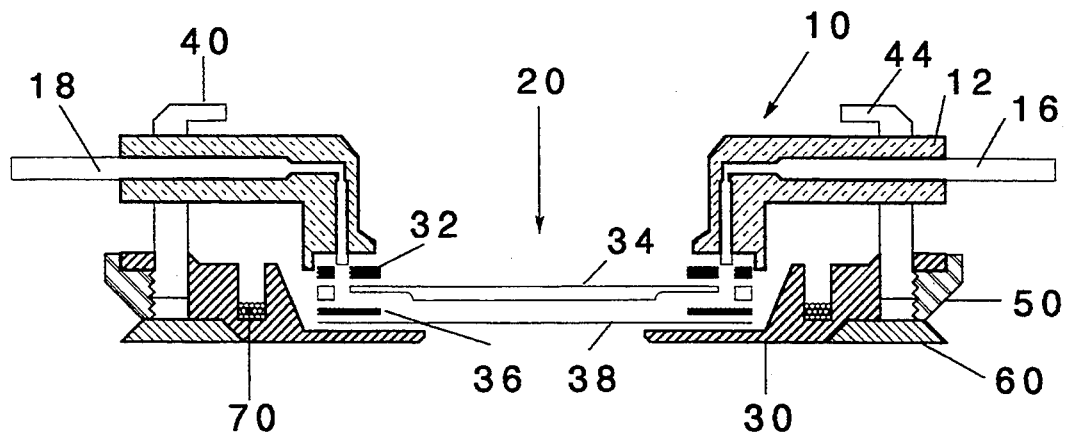
FIG. 12 is a sectional! somewhat diagrammatic and somewhat exploded view in elevation of the elements of FIGS. 2-11, showing the elements assembled and containing and securing the upper seal unit, the cover slip, the infusion/perfusion unit, and lower gasket unit of FIG. 1.

The chamber base unit 30 mated or coupled with the chamber frame unit 12 will house an upper seal 32, cover slip window or infusion/profusion unit 34, a lower gasket 36, and another cover slip window referred to as cover slip 38, with these units, as shown in FIG. 1 and diagrammatically in FIG. 12 being constructed and arranged to form an infusion/perfusion chamber in communication with the infusion/perfusion ports 16 and 18. My U.S. Pat. No. 4,974,952 earlier referred to clearly describes the function of the infusion/perfusion chamber and such description is incorporated herein by reference.

The present invention lies in the securing and locking assembly 40 for locking the chamber frame unit 12 with the chamber base 30, and includes a ring shaped upper unit 42 formed with machine threads on the outer periphery thereof, and four identically shaped equally arcuately spaced, upwardly, axially extending L-shaped fingers 44, each pair being spaced 90° apart. The upper unit 42 is threaded into a ring shaped lower base member 50 having complementary internal threads formed on its interior periphery. The assembled upper unit 42 and lower base member 50 are rotatably received on the outer radial portion of the chamber base unit 30 as is shown in FIG. 12. When assembled with the chamber base unit 30, the upwardly extending fingers 40 of the securing and locking assembly 40 extend through arcuately spaced axially extending openings 54 which are axially aligned with the notches 14 formed on the chamber frame unit 12, with the fingers 44, in turn, extending through the opening 54 into radial alignment outside the notches 14. The fingers 44 and the notches 14 are sized and shaped such that the radially extending portions of the fingers 44 will engage the upper surfaces of the chamber frame unit 12 when the upper unit 42 is rotated relative to the lower base member 50. The circumferential lengths of the openings 54 are greater than the circumferential lengths of the notches 14 for the reason to be understood as this description continues. The relative rotation of the upper unit 42 and lower base member 50 will occur as follows: when desiring to secure and lock the chamber frame unit 12 and chamber base 30 together the lower base member 50 will be rotated by hand, carrying with it the upper unit 42 until the upwardly extending portions of the fingers 44 engage the axial surfaces of the openings 54 thereby stopping the rotations of the upper unit 42 with the lower base member 50 continuing to be rotated on the threads between the upper unit 42 and the lower base member 50 whereby the entire upper unit 42 will translate axially downwardly and the radial portions of the fingers 44 will engage upper portions:of the chamber frame unit 12. The result will be that the chamber frame 12 and the chamber base 30 will be secured and locked to each other. When the fingers 44 engage the sides of the openings 54 the fingers 44 will be positioned arcuately beyond the notches 14 and in a position to engage upper surface portions! of the chamber frame unit 12. To disengage the chamber frame unit 12 and chamber base 30, the lower base member 50 is rotated in the opposite direction and will translate axially upwardly on the threads between the upper unit 42 and the lower base member 50 raising the fingers 44 above the chamber frame 12, and thereafter both the lower base member 50 and upper unit 42 will rotate as a unit to position the fingers 44 relative to the notches 14 such that the chamber frame 12 and chamber base 50 are in position to be separated.

Figure 6:
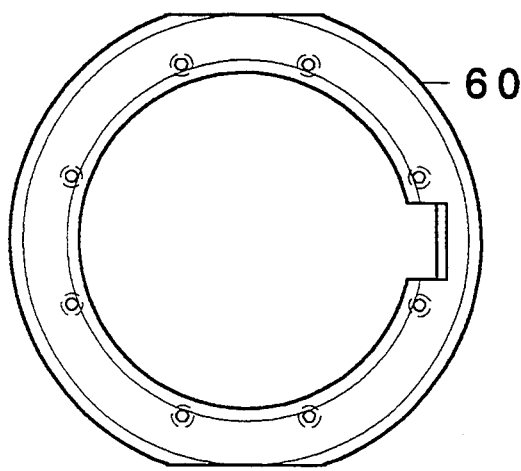
FIG. 6 is a plan view of the base element forming part of the chamber base of FIG. 1, and not illustrated in FIG. 1.
Figure 5:
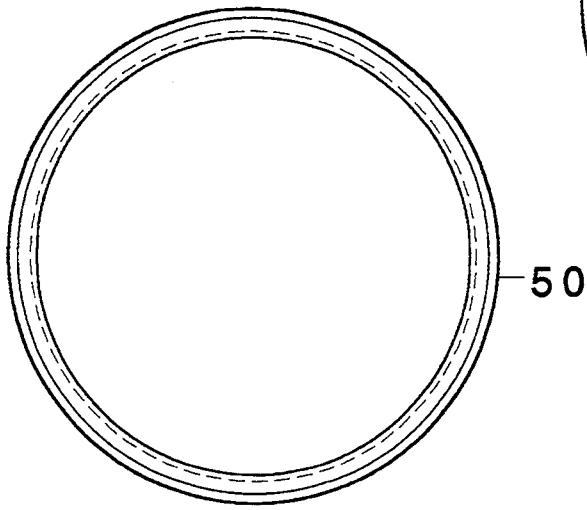
FIG. 5 is a plan view of another element of the rotatable ring assembly of the securing and locking assembly of the present invention, showing details not illustrated in FIG. 1.
Figure 7:
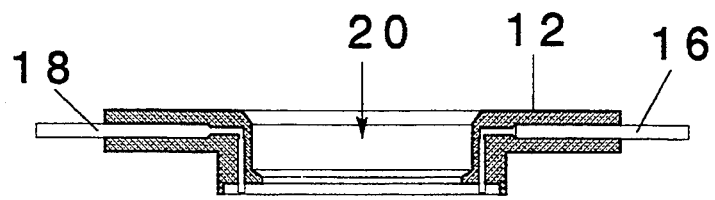
FIG. 7 is a sectional view in elevation of the chamber frame unit of FIG. 2.
Figure 8:
FIG. 8 is a sectional view in elevation of the chamber base of FIG. 3.
Figure 9:
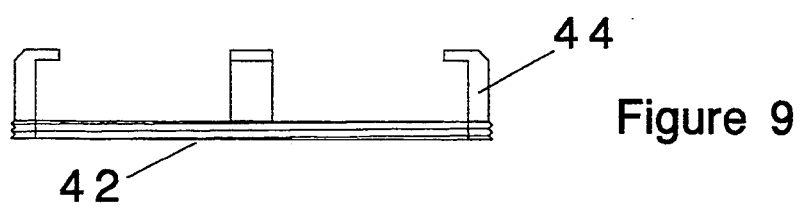
FIG. 9 is an elevation view of the element of FIG. 4.
Figure 10:
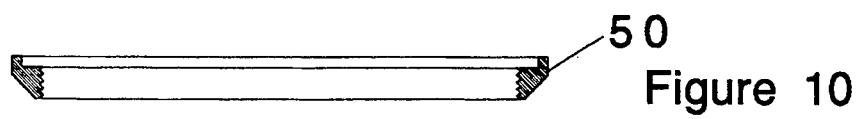
FIG. 10 is a sectional view in elevation of the element of FIG. 5.
Figure 11:
FIG. 11 is an elevation view of the base element of FIG. 6.

FIGS. 6, 11 and 12 show a base ring 60 shaped and sized to fit into an annular channel formed in the lower portion of the chamber base 30. The base ring 60 is secured to the chamber base 30 by machine bolts, not shown, and secures in place the securing and locking assembly 40 with the chamber base 30.

FIG. 12 is somewhat diagrammatic and is exploded in its representation, with the elements of the live cell chamber 10 being separated for description purposes only. In actuality when the elements of the live cell chamber 10 are assembled the inner elements are snugly operatively engaged to form an infusion/profusion chamber with the infusion/profusion fluid ports 16 and 18 communicating with the chamber.

The chamber base 30 is also formed to receive a toroidal shaped heater element 70 which may be electrically activated to provide controlled heat energy as desired to the assembly.

The securing and locking assembly 40 is simply hand operated and provides positive and uniform clamping and locking of the chamber base 30 to each other. The internal elements, and in particular the fragile infusion/profusion unit 34 and cover slips 38, are protected against damage and misalignment between engaged elements avoided to preserve sealing therebetween.

It should now be clearly recognized how the present invention overcomes the drawbacks of the heretofore method and means of securing chamber frame units and chamber bases together. Other modifications to the elements forming the present invention might also be recognized be those skilled in this art. Those skilled in this art should also understand that this invention is applicable to any live cell chamber and is not limited to my live cell chamber described and claimed in my U.S. Pat. No. 4,974,952. The recitation of the elements in the claims hereof are intended to apply to any live cell chamber.

While I have shown and described a present preferred embodiment of this invention,: it is to be distinctly understood that the invention is not limited thereto, but may be otherwise embodied within the scope of the following claims.

I claim:

1. In a live cell chamber apparatus for studying live cells in culture medium with a microscope including a chamber frame unit, a chamber base unit, first and second coverslip windows and sealing units operatively associated with said coverslip windows forming a chamber thereof, the improvement therewith of a securing and locking assembly comprising:
    mating means for coupling said chamber frame unit and said chamber base unit together, thereby forming an enclosure, and
    securing means for uniformly securing and locking said enclosure upon rotation thereof through a pre determined arcuate distance, and for unlocking said enclosure upon reverse rotation the same arcuate distance.

2. The securing and locking assembly as set forth in claim 1 wherein said securing means includes a rotatable ring assembly disposed on said chamber base unit and having at least a pair of upright extending finger members arranged to lockably engage upper portion of said chamber frame unit upon rotation of said ring assembly.

3. The securing and locking assembly as set forth in claim 1 wherein said securing means includes a rotatable ring assembly disposed on said chamber base unit and having at least a pair of upright extending finger members arranged to engage and tighten said chamber frame unit onto said chamber base unit upon rotation of said ring assembly a first and second predetermined arcuate distance, wherein, upon rotation of said ring assembly through said first predetermined arcuate distance said finger members engage upper portion of said chamber frame unit then cease rotational movement and upon further rotation of said ring assembly through said second predetermined arcuate distance said finger members will draw down and tighten said chamber frame unit onto said chamber base unit.

4. The securing and locking assembly as set forth in claim 2 wherein said chamber frame unit and said chamber base unit are generally circular in shape, and said chamber frame unit having at least a pair of diametrically opposed radially extending recesses, and said finger members are arranged to be received radially of said recesses and to engage said upper portions of said chamber frame unit arcuately adjacent to said recesses upon rotation of said ring assembly.

5. The securing and locking assembly as set forth in claim 4 wherein said recesses and said finger members are symmetrically spaced.

* * * * *